(12) United States Patent
Quan et al.

(10) Patent No.: US 6,180,133 B1
(45) Date of Patent: Jan. 30, 2001

(54) ANTIOXIDANT COMPOSITION FOR TOPICAL/TRANSDERMAL PREVENTION AND TREATMENT OF WRINKLES

(75) Inventors: Danyi Quan; Srinivasan Venkateshwaran; Charles D. Ebert, all of Salt Lake City, UT (US)

(73) Assignee: Watson Pharmaceuticals, Inc., Corona, CA (US)

( * ) Notice: Under 35 U.S.C. 154(b), the term of this patent shall be extended for 0 days.

(21) Appl. No.: 09/198,734

(22) Filed: Nov. 24, 1998

Related U.S. Application Data
(60) Provisional application No. 60/066,868, filed on Nov. 25, 1997.

(51) Int. Cl.$^7$ .......................... A61K 9/70; A61K 31/045; A61K 31/13; A61K 31/16; A61K 31/19; A61K 31/34; A61K 31/355; A61K 31/375; A61K 31/40

(52) U.S. Cl. ................... 424/448; 424/78.02; 424/195.1; 424/443; 424/444; 424/445; 424/447; 424/449; 514/23; 514/54; 514/62; 514/159; 514/263; 514/359; 514/408; 514/423; 514/424; 514/428; 514/458; 514/474; 514/553; 514/557; 514/561; 514/563; 514/579; 514/725; 514/772; 514/772.2; 514/772.3; 514/772.4; 514/777; 514/783; 514/844; 514/848; 514/975

(58) Field of Search ...................... 514/458, 474, 514/725, 159, 183, 359, 408, 423, 424, 428, 553, 557, 561, 563, 579, 263, 54, 42, 23, 772, 772.2, 772.3, 772.4, 777, 783, 844, 848, 975, 62; 424/195.1, 449, 443, 447, 448, 444, 445, 78.02

(56) References Cited

U.S. PATENT DOCUMENTS

| | | | |
|---|---|---|---|
| 4,584,355 | * 4/1986 | Blizzard et al. | 525/477 |
| 4,855,294 | * 8/1989 | Patel et al. | 514/212 |
| 5,254,331 | 10/1993 | Mausner | 424/59 |
| 5,470,874 | 11/1995 | Lerner | 514/474 |
| 5,516,793 | * 5/1996 | Duffy | 514/474 |
| 5,529,769 | 6/1996 | Cho et al. | 424/74 |
| 5,785,978 | 7/1998 | Porter et al. | 424/401 |

FOREIGN PATENT DOCUMENTS

| | | |
|---|---|---|
| WO 96/14822 | 5/1996 | (WO) . |
| 96/16642 | * 6/1996 | (WO) . |

OTHER PUBLICATIONS

Fedok, "The Aging Face", Facial Plastic Surgery, vol. 12, No. 2, pp. 107–115. Apr. 1996.

Sakuroaka et al., "Analysis of connective tissue macromolecular components in Ishibashi rat skin: Role of collagen and elastin in cutaneous aging", Journal of Dermatological Science, vol. 12 pp. 232–237. 1996.

Bailey et al., "Biological significance of the intermolecular crosslinks of collagen", Nature, vol. 25, Sep. 13, 1974.

Lkigman et al., "The Contributions of UVA and UVB to Connective Tissue Damage in Hairless Mice", Journal of Investigative Dermatology, vol. 84 pp. 272–276, 1985.

Wehr et al., "Controlled two–center study of lactate 12 percent lotion and a petrolatum–based cream in patients with xerosis", Therapeutics for the Clinician pp. 205–209. Mar. 1986.

Grove, "The effect of moisturizers on skin surface hydration as measured in vivo by electrical conductivity", Current Therapeutic Research, vol. 50, No. 5. Nov. 1991.

Maeda et al., "Effects of Chronic Exposure Ultraviolet–A Including 2% Ultraviolet–B on Free Radical Reduction Systems in Hairless Mice", Photochemistry and Photobiology, vol. 54, No. 5 pp. 737–740. 1991.

Lavker et al., "Effects of topical ammonium lactate on cutaneous atrophy from a potent topical corticosteroid", Journal of the American Academy of Dermatology, vol. 26, No. 4 pp. 535–544. Apr. 1992.

Breener, "The Efficacy of 12 percent ammonium Lactate in the Treatment of Dry Skin of the Feet: A Clinical Product Review", Current Podiatric Medicine vol. 37, pp. 15–17. Aug. 1988.

Smith, "Epidermal and dermal effects of topical lactic acid", Journal of the American Academy of Dermatology, vol. 35, No. 3, Pt. 1, pp. 388–391. 1996.

Lawrence et al., "Glycolic Acid Modulation of Collagen Production in Human Skin Fibrolast Cultures in Vivo", American Society for Dermatologic Surgery, Inc., vol. 22 pp. 439–441. 1996.

Gilchrest, "Treatment of photodamage with topical tretinoin: an overview", Journal of American Academy of Dermatology, vol. 36, No. 3, Part 2. pp. S27–S36. Mar. 1997.

Murad et al., "The Use of Glycolic Acid as a Peeling Agent," Cosmetic Dermatology, vol. 13, No. 2, pp. 285–307, Apr. 1995.

Perricone, "The Use of Topical Ascorbyl Palmitate and Alpha Lipoic Acid for Aging Skin", DCI, pp. 20–24. Feb. 1998.

\* cited by examiner

Primary Examiner—John Pak
Assistant Examiner—Frank Choi
(74) Attorney, Agent, or Firm—Thorpe, North & Western, LLP

(57) ABSTRACT

An anti-wrinkle skin treating composition comprises a pressure sensitive matrix patch having dissolved in the adhesive a mixture of antioxidants in the form of a Vitamins C ester and Vitamin E. Also preferably dissolved in the adhesive are glycerine and a polydiorganosiloxane adhesion-adjusting agent. Optionally dissolved in the adhesive is also one or more members selected from the group consisting of moisturizing agents, skin collagen synthesis promoting agents and exfoliating agents. When applied to a wrinkled skin area the composition acts to diminish fine wrinkles and improves the overall thickness, elasticity, firmness and smoothness of the skin. The modified adhesive properties of the patch are sufficient to maintain the patch in place on the skin for the recommended treatment period while allowing the patch to be readily removed without causing skin irritation or leaving adhesive residue on the skin.

22 Claims, No Drawings

US 6,180,133 B1

ANTIOXIDANT COMPOSITION FOR TOPICAL/TRANSDERMAL PREVENTION AND TREATMENT OF WRINKLES

This application claims the benefit of U.S. Provisional Application Ser. No. 60/066,868 filed Nov. 25, 1997.

BACKGROUND AND PRIOR ART

This application is directed to an improved skin cream composition for the treatment and minimization of the appearance of wrinkles and a method for the transdermal delivery thereof.

Physical appearance, beauty, and the desire to maintain youthfulness are concepts that are not new. In all societies around the world, there are easily recognizable incentives regarding the maintenance of a favorable appearance. The nature and form of desirable appearance varies, but each culture has developed its own standards and norms. In our modern society, psychologists, sociologists, and economists, as well as those on Madison Avenue, have made observations about our attitudes regarding appearance. Cosmetologists, health experts, personal trainers, and cosmetic surgeons have supplied us with various means by which we can maintain our youthful appearance and improve the undesired and undesirable changes of aging. Aging and aging of the face are the results of many factors. Some of these are intrinsic, some extrinsic. Some are controllable, some uncontrollable. The rate at which different people age is variable. Aging on a biologic basis is not a homogenous, even-flowing process, but appears to evolve with various accelerations and decelerations. Individuals appear to age at different rates; however, we all age in a similar progression, and therefore discernable patterns emerge.

The aging process is believed to be based on the same principles in every individual. The intrinsic aspects of aging are largely based on heredity; these are programmed into the individual at the cellular level and are largely unalterable. The extrinsic factors are the results of an individual's habits, nutrition, and exposure to deleterious factors, such as cigarette smoking and ultraviolet sunlight. The individual can influence or control the extrinsic factors largely by avoidance and through the maintenance of good health habits and exercise. Once the observable changes of aging have occurred, few are reversible. Many of the changes, however, can be improved through makeup, cosmetic skin care, and cosmetic rejuvenative surgery.

Histologically, sun-damaged epidermis is significantly thickened and disorganized as compared to non-damaged skin. In response to long-term exposure to sun, epidermal melanocytes enlarge, proliferate and migrate to higher levels of the epidermis. Chronic stimulation of melanocyte often leads to dyschromia, spotty hyper pigmentation, and the proliferation of pigmented keratosis. It is also known that ultraviolet radiation causes extensive damage to both cellular and structural components of the dermis.

Nutritionists have long warned about the deleterious effects of free radicals. Indeed it has been well documented that significant damage to biological tissues results from free radical induced oxidation. The presence of oxidation inducing free radicals is promoted by exposure to several environmental factors. Among these factors are air pollutants, ultraviolet radiation, diet and cosmetic agents. Dermatologically, the presence of free radicals promotes and sometimes accelerates the aging process. One result of this acceleration would be the observance of wrinkles. Indeed, similar concerns regarding free radical induced damage to the skin has as well been documented.

The genetically determined process of the aging skin results in a predictive group of morphologic and physiologic changes. In the skin of an aged person, the epidermis is of variable thickness, there is modest diversity in cell size and shape, the dermatoepithelial abutment is flattened and rete ridges are lost, cumulatively rendering aged skin fragile and susceptible to injury from sheering forces. The dermis of senescent skin is characterized by marked cellular atrophy and a corresponding reduction in metabolic activity. As a result, the percentage of newly synthesized collagen in the dermis decreases. As a result, aged or aging skin is less distensible, poorly resilient, and prone to fine wrinkling. Furthermore, in aging skin the epidermis thins with a gradual loss of rete ridges and concomitant decrease in cell turnover in the basal cells. Furthermore, the surface corneocyte layer thickens with age. The dermis also becomes thinner with decreased collagen content, degeneration of elastic fibrils, decreased water content, and the gradual addition of stable cross-links in and between collagen fibrils. Skin thickness in women reaches maximum at approximately age 35 and decreases gradually thereafter. In men, the skin thickness versus age curve is different, with the peak in skin thickness occurring at age 45. With these changes, there is a loss of the biomechanical properties of the skin and with advancing age, the ability of the skin to recover from the initial stages of deformation drops. The appearance of aged, sun-damaged skin is therefore the result of these intrinsically and extrinsically caused changes. The skin may have uneven pigmentation and an uneven texture, may be wrinkled, less distensible, and more prone to laxity.

Fine wrinkles generally begin to appear in individuals in their twenties; these wrinkles deepen as individuals approach their thirties. In the upper face, crow's feet and wrinkling above the eyelids may occur as early as the late twenties. The formation of crow's feet is secondary to the contraction of the orbital portion of the orbicularis oculi muscle and they are accentuated by the elevation of the upper cheek by the zygomaticus and the zygomatic head of the quadratus labii superioris muscle.

Chronic exposure to ultraviolet light damages structural and functional components of the skin. The resulting photo-damage, or photo-aging as it is sometimes called, is characterized by wrinkling, sallowness, modeled hyper pigmentation, and laxity. Histologically, photo-damage is accompanied by epidermal thinning, variable atypia, large, irregular grouped melanocyte and elastosis. In 1986, Kligman et al. reported that tretinoan cream (Retinin-A), which had been used for more than twenty years in the treatment of acne vulgaris, could also produce a more attractive, less-wrinkled skin in older patients. When applied to persons with photo-damaged skin, tretinoan cream proved effective in partially reversing structural skin damage. In the past ten years, clinical and histologic studies have confirmed the efficacy of tretinoan as therapy for smoothing skin texture, reducing wrinkles, and improving skin discoloration. Further research by Kligman et al. studied the efficacy of topical tretinoan cream on reversing facial skin photo-damage. Elderly patients received a daily facial application of 0.05% tretinoan cream for six to twelve months and six age-matched subjects received a placebo vehicle only. Although clinical changes were deemed to be slight, many histologic effects were observed in skin biopsy specimens. One of the clinical changes observed from this research included normalization of various skin structures such as thickening of a previously atrophic epidermis, elimination of dysplasia and atypia, and more uniform dispersion of melanin and the formation of new dermal collagen and blood vessels. Furthermore, topical tretinoan has been shown to have beneficial effects in the treatment of hyper pigmented lesions of a variety of types such as those associated with photo-damage in white patients, and those caused by inflammation or melasma in black patients. Additionally, "liver spots" on the face or upper extremities of patients with photo-damage were treated with 0.1% tretinoan cream daily, resulting in a lightening of the liver spots (more appropriately called hyper pigmented macules or also termed actinic lentigines). However, tretinoan frequently induces mild to moderate dermatitis. Although, percutaneously absorbed tretinoan has no detectible effect on plasma concentrations of the drug and its metabolites in any of the protocols reported, many patients see the induced mild to moderate dermatitis as prohibitively discomforting for effective use in correction of wrinkles.

Much work has been directed towards the use of topically applied organic acids, which cause a destruction and subsequent removal of the outer dermis layers, thereby provoking the formation of new collagen. It is believed that the induced formation of new collagen would occur preferentially over old collagen, thereby replacing wrinkles with new, young dermis in the absence of said wrinkles. Previous works with chemical peels, as they are known, discuss the post-peel development of a zone of collagen. The zone of collagen is a deposit of a new collagen that is laid down in the upper dermal layers after a chemical peel. Both phenol and trichloracetic acids (TCAs) have been histologically studied to compare the amount of new deposition in the zone of collagen. The deeper depth of necrosis caused by the chemical peeling agent resulted in a deeper zone of collagen. Thus, more damaging chemical peels can smooth deeper layers of the skin. For instance, higher concentrations of trichloracetic acid, perhaps 50–70%, can penetrate to layers of the reticular dermis and also cause a zone of new collagen to that same depth. However, higher concentrations of trichloracetic acid can lead to scarring, and other severe risks involved with trichloracetic acid use. Although it is true that trichloracetic acids may be applied at a lesser concentration, the same types of risks are involved as are present with a higher concentration because of the inherent strength of the acid involved.

α-Hydroxy acids (AHAs) have been used for many years as exfoliants, moisturizers, and emollients. Lactic acid salts, most notably sodium lactate, have been hypothesized to be part of the skin's own natural moisturizing system. In addition, AHAs and salicylic acid, a structurally similar β-hydroxy acid, have been used for at least 40 years as peeling agents.

Studies have shown that several AHAs (as well as β-hydroxy and carboxylic acids) in low concentration (5%) stimulate epidermal turnover or cell renewal (exfoliation) and have the potential to irritate the skin. This activity is closely linked to acidic pH as neutralized acids lose their ability to exfoliate the skin.

The moisturizing activity of AHAs and their ability to exfoliate the skin and interfere with intercellular cohesion in the outer epidermis are well documented. It is suggested that AHAs interfere with cohesion in the stratum granulosum, unlike salicylic acid and other exfoliants.

Several studies on the activity of a buffered 12% ammonium lactate lotion have documented its moisturizing activity (Wehr et al. *Controlled two-center study of lactate 12 percent lotion and a petrolatum-based cream in patients with xerosis*, Cutis, 37:205–9 (1986); Grove, *The effect of moisturizers on skin surface hydration as measured in vivo by electrical conductivity*, Curr. Ther. Res. Clin. Exp., 50:712–9 (1991); and Breener, *The efficacy of 12 percent ammonium lactate in the treatment of dry skin of the feet. A clinical product review*, J. Curr. Podiatr. Med., 37:15–7 (1988)). Lavker et al., *Effects of topical ammonium lactate on cutaneous atrophy from a potent tropical corticosteroid*, J. Am. Acad. Dermatol., 26:535–44 (1992), found that ammonium lactate caused an increase in dermal ground substance and increased glycosaminoglycan synthesis. Murad et. al., *The use of glycolic acid as a peeling agent, Dermatological Clinic on Cosmetic Dermatology*, Murad H, editor, Philadelphia: WB Saunders, (1995), demonstrated that aggressive glycolic acid peels significantly increase collagen and dermal ground substance. Precisely how and why AHAs produce these effects is not known.

Vitamin C (ascorbic acid) is alleged to protect the brain and spinal cord from free radicals. It promotes collagen (connective tissue) synthesis, lipid (fat) and carbohydrate metabolism, and the synthesis of neurotransmitters. It is also essential for optimum maintenance of the immune system. Vitamin C is toxic to a wide range of cancer cells, especially melanoma. The oxidizing enzyme tyrosine that catalyzes the aerobic action of tyrosine into melanin and other pigments is also inhibited by the presence of Vitamin C. Vitamin C has been found to be effective in catalyzing the immune response to many viral and bacterial infections. Besides the many applicable uses set forth above, Vitamin C is essential for collagen synthesis and wound healing. International patent application, WO 96/14822, published May 23, 1996, and corresponding U.S. Pat. No. 5,785,978, issued Jul. 28, 1998, teach that concentrated dry powdered antioxidants, Vitamin C and its salts in particular, may be compounded with adhesives and applied to target areas where wrinkles develop to ameliorate photo, oxidative and stress damage and improve skin appearance. However, it is to be noted that only the use of ascorbic acid is shown and the adhesive/ascorbic acid compositions illustrated resulted in adhesive remaining on the skin of the wearer when a patch containing the adhesive composition was removed. Also, application of such patches to sensitive areas, such as around the eyes, often results in pain and trauma during the removal process.

Modern environmental conditions, such as heating and air conditioning, exposure to the sun, and environmental pollution exert severe stress on the skin and accelerate the natural aging process resulting in wrinkles, decreased firmness and elasticity, dryness and other cosmetically undesirable effects. Although a number of skin cream compositions already exist, there is a need for a simple-to-apply and effective all-in-one cosmetic treatment, such as a skin preparation that can counteract and minimize, simultaneously, distresses on the skin and improve firmness and elasticity while it counteracts dryness so that wrinkles and other undesirable effects appearing on the skin are corrected or at least delayed.

Many formulations have been developed which focus on a few accepted skin treatment regimes. Moreover, many of the available skin treatment systems do not adequately prevent and treat the multitude of hazards which deleteriously impact the skin.

OBJECTS OF THE INVENTION

Therefore it is an object of this invention to provide a matrix-type patch to provide significant free radical protection to the skin by means of a pressure-sensitive adhesive having dissolved therein a combination of a Vitamin C ester, Vitamin E, glycerine, an adhesion adjusting agent and, optionally, one or more members selected from the group consisting of a skin moisturizer, a collagen synthesis promoting agent and an exfoliating agent.

An additional object of the present invention is to provide a method for the transdermal delivery of a skin wrinkle diminishing composition which provides significant free radical protection by means of a combination of a Vitamin C ester, Vitamin E, glycerine and optionally one or more members selected from the groups consisting of a moisturizing agent, a collagen synthesis promoting agent and an exfoliating agent.

The combination of Vitamin C esters, Vitamin E and other ingredients, such as moisturizers, collagen synthesis promoting agents and exfoliating agents, are preferably dissolved in a pressure-sensitive adhesive layer of a matrix patch type delivery system. Such patches contain an occlusive backing layer to which the pressure-sensitive layer is adhered. A peelable layer is contained on the adhesive opposite the impermeable backing and is stripped from the patch so that the adhesive layer can be applied transdermally over the skin.

These and other objects of the invention will become more apparent from the following description and examples.

SUMMARY OF THE INVENTION

A transdermal skin composition according to the present invention ameliorates the concerns not adequately addressed by the skin treatment regimes disclosed in the prior art. The skin treating compositions of the present invention act to prevent or correct deleterious effects on the skin, such as stress, sensitivity and various irritations thereby improving firmness and elasticity of the skin, increasing effectiveness of the skin as a barrier against external aggressions, diminishing fine wrinkles and improving the overall thickness, firmness and smoothness of the skin. Additionally, skin which is subjected to the benefits of the presently disclosed composition will be significantly hydrated and moisturized. The skin treating compositions of the present invention comprises Vitamin C esters, Vitamin E, and optionally, alpha-hydroxy acids, such as lactic and glycolic acids and other keratinolytics for the treatment or prevention of wrinkles and skin dryness.

Vitamin C is present as an ester of L-Ascorbic acid. L-Ascorbic Acid 6-Palmitate (ascorbyl palmitate) is particularly preferred. Ascorbyl palmitate differs from ascorbic acid and its salts in various ways. Ascorbyl palmitate is a synthethic ester which is fat soluble in contrast to ascorbic acid and its salts which are water soluble. This ester forms ascorbyl palmitate which is stable, compatible with other skin treating agents and has a neutral pH as opposed to ascorbic acid which has a very low pH. Due to its fat solubility, ascorbyl palmitate penetrates the skin more readily than ascorbic acid and its salts reaching comparativelly high levels in much shorter periods of time.

Because of its skin penetration properties, ascorbyl palmitate is a powerful antioxidant and anti-inflammatory with the cell structure preventing free radical damage. Ascorbyl palmitate also is more effective than the more traditional forms of Vitamin C in promoting collagen production. Ascorbyl palmitate acts together with Vitamin E as an anti-oxidant and anti-inflammatory in preventing skin damage and reducing effects of aging, such as wrinkle production.

Any suitable form of Vitamin E may be utilized, e.g. $\alpha$, $\beta$, $\gamma$-tocopherols preferably in the from of an alcohol, ether or ester. Most commonly used are d,l-$\alpha$-tocopherol, d,l-$\alpha$-tocopherol acetate and d-$\alpha$-tocopherol acetate.

The following definitions will be useful in describing the invention and will eliminate the need for repetitive explanations.

By "transdermal" is meant transdermal or percutaneous administration, i.e. application of the skin treating composition directly to the skin to be treated. Hence the terms "skin," "derma," "epidermis," and the like shall also be used interchangeably unless specifically stated otherwise.

By the term "matrix," "matrix patch" or "matrix system" is meant the essential skin treating components combined in a biocompatible pressure-sensitive adhesive, also containing an adhesion-adjusting agent, which may or may not also contain other ingredients. A matrix system is usually an occlusive adhesive patch having an impermeable film backing and, before transdermal application, a release liner on the surface of the adhesive opposite the film backing.

In matrix systems, the adhesive is present in amounts ranging from 60 to 99.5% by weight and will preferably be present in amounts of between about 70 and 95% by weight. Adhesion adjusting agents, such as polydiorganosiloxanes, are combined with the adhesive in amounts ranging from about 0.1 to 10% by weight.

The antioxidant Vitamin C is an L-ascorbic acid ester and Vitamin E may each be present in amounts ranging between about 0.1 and 10% by weight and preferably between about 0.1 and 5%. Most preferably these vitamins will be present in amounts of between 0.1 and 2%. The Vitamins C ester and Vitamin E may be present in equal amounts (1:1 ratio) or may be present in varying weight ratios of between about 0.1:10 to 10:0.1. Additionally, moisturizing agents such as $\alpha$ and $\beta$-hydroxy acids, 2-pyrollidone-5-carboxylic acid (PCA) and its salts and esters, may be present in amounts of between about 0.1 and 10% by weight. Other ingredients such as Vitamin A and Vitamin A esters, salicylic acid and its salts, caffeine, hyaluronic acid, herbs and botanic extracts may be incorporated, each in amounts of between about 0.1 and 10 and preferably between about 0.1 and 5.0% by weight. The only limiting factor, other than functionality, is that the total concentration of ingredients in the pressure-sensitive adhesive is below the saturation level, i.e. that the ingredients in the adhesive are dissolved and are not present in crystalline or solid form.

Additionally, glycerin, which is also a moisturizing agent, may be added as an anti-irritant or to modulate the delivery of the other skin treating agents and may be present in amounts of from 0 to 15% by weight. When used, glycerin is present in amounts of between about 0.1 and 10%.

In summary, in the matrix system, the carrier is primarily the pressure-sensitive adhesive in which the adhesion adjusting agent and all of the other ingredients are dissoslved.

Suitable pressure-sensitive adhesives may include acrylic copolymer adhesives or "acrylic adhesive," rubber-based adhesives or "rubber adhesive," and ethylene vinyl acetate copolymer adhesives. However, any other suitable pressure-sensitive adhesives may also be used which are compatible with the skin treating agents as utilized.

It has been found that the combination of the pressure-sensitive adhesive and adhesion-adjusting agent permits satisfactory adhesive properties that matrix patches can be applied to an area of skin to be treated with sufficient adhesiveness to remain on the skin for a treatment period, generally ranging from about an hour but usually not more than overnight. Generally the treatment period will be between about four and eight hours. When the patch is removed, the adhesive is peeled from the skin without leaving significant adhesive residue on the treated area. Further, the presence of glycerine in the formulation serves as an anti-irritant and moisturizing agent.

In such formulations, the transdermal delivery of antioxidants to the treated skin is optimized and any side effects, such as skin irritation and patch residue are minimized.

The combined properties of Vitamin C esters and Vitamin E delivered transdermally from a matrix-type patch is much more effective than a series of applications of these vitamins applied to the skin surface by hand as a cream, ointment or lotion.

EXAMPLES AND PREFERRED EMBODIMENT

Skin care experts believe that natural antioxidants may help protect skin against the ravages of pollution and sunlight, which contribute to wrinkles by breaking down the skin's outer membranes. The anti-wrinkle matrix patches of the present invention, which may be worn for short periods, i.e. minutes or hours or even up to overnight, work well on fine lines and wrinkles. The preferred embodiment is a matrix patch which comprises an impermeable backing having bonded thereto an adhesive layer consisting of a pressure-sensitive adhesive having homogeneously blended and dissolved therein effective amounts of Vitamins C esters, Vitamin E, an adhesion-adjusting agent, glycerine and, optionally, herbs and/or botanic extracts, moisturizers such as α and β-hydroxy acids and other skin-care ingredients. A peelable layer sandwiches the adhesive layer opposite the impermeable backing and is removed when the patch is applied to the skin. One significant benefit derived from use of a patch for administration of the skin care composition of the present invention is the enhanced absorption of the therapeutic components into the skin in need thereof.

Because the matrix patch is to be worn for a selected, but limited time, perhaps overnight, and is applied to sensitive skin sites, such as around the eyes, it is important that the matrix patch be attached to the skin with lighter adhesive properties than other pressure-sensitive adhesive matrix patches adapted for prolonged usage. Such adhesive adjusted patches can therefore be removed with less force than other more conventional pressure-sensitive adhesive patches. Hence, there is a need for an adhesion adjusting agent which facilitates early patch removal without significant skin damage and without leaving significant adhesive residue when the patch is removed. This is attainable by means of the blending into the adhesive of an effective amount of a polydiorganosiloxane as noted above.

Polydiorganosiloxanes as a class may be utilized as more fully described below. Of that class the polydimethylsiloxanes are particularly preferred and are specifically exemplified. Polydimethylsiloxane polymers and copolymers are also known by the generic name dimethicone. These terms will be used interchangeably throughout this description.

By "polydiorganosiloxane polymer" is meant a silicone fluid polymer having repeat units of the formula $R_2SiO_{2/2}$ siloxy units where R is a hydrocarbon or substituted hydrocarbon having from about 1 to 20 carbons atoms and is represented by Formula 1:

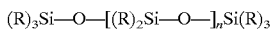

$$(R)_3Si\!-\!O\!-\![(R)_2Si\!-\!O\!-\!]_nSi(R)_3 \quad \text{FORMULA I}$$

where R can be a hydrocarbon or substituted hydrocarbon of 1 to about 20 carbon atoms and can be selected from the group consisting of alkyl, aryl, cycloalkyl and the like which may be substituted to contain halogen, amino, hydroxy, ether or other similar functionalities. The integer "n" is sufficient to cause the silicone fluid to have a viscosity of between about 20 and 25,000 centistokes. Preferably the viscosity will be between about 20 and 12,500 centistokes.

Polydiorganosiloxane polymer fluids may be generally classified as unmodified silicones, linear and cyclic volatile silicones, alkyl/alkoxy modified silicones, phenyl modified silicones, aminofunctionalized silicones, polyglucoside silicones and polyether functionalized silicones.

Within the various classes the polydiorganosiloxane polymer fluids are represented by proprietary tradenames including a number which is generally, but not always, indicative of viscosity.

Representative proprietary polydiorganosiloxane follow.

Exemplary of unmodified silicone fluid polymers are Dimethicone and Dimethiconol available as SP 96®(20, 50-1000), Visasil®(5M-100M) and SF18(350) from Costec Inc. (Palatine, Ill.), Dow Corning® 200 and 225 fluids from Dow Corning Corporation (Midland, Mich.), DM 100-1000, AK 5-1MM, X-345 and F-1006 from Wacker Silicones Corporation (Adrian, Mich.) and Sentry Dimethicone NF from Whitco Corporation (Greenwich, Conn.).

Representative of linear and cyclic volatile silicones are Cyclomethicone (>4) available as SF 1173, SF 1202 and SF 1204 from Costec Inc., Dow Corning® 244, 145, 344 and 345 fluids from Dow Corning Corporation and CM 040 from Wacker Silicone Corporation; Dimethicone SF96® (5) from Costec Inc. and DM 1 plus from Wacker Silicones Corporation; Hexamethyldisiloxane available as DM 0.65 from Wacker Silicones Corporation.

Typical of alkyl/alkoxy modified silicones include lauryl dimethicone available as Dow Corning® Q2-5200 from Dow Corning Corp, LDM 3107VP from Wacker Silicones Corp.; Cetyl dimethicone available as Dow Corning® 2502 from Dow Corning Corp. and DMC 3071 from Wacker Silicones Corp.; Stearyl dimethicone available as SF1632 from Costec, Inc., Dow Corning® 2504 from Dow Corning Corp., and E32 from Wacker Silicones Corporation.

Illustrative of phenyl modified silicones are Phenyltrimeticone available as SF 1550 from Costec Inc., Dow Corning® 556 fluid from Dow Corning Corporation and PDM 20, 100, 1000 from Wacker Silicones Corporation.

Aminofunctionalized silicones may be represented by Amodimethicone available as SM2658 from Costec, Inc., Dow Corning® 929 and 939 from Dow Corning Corp. and L650, 652 and ADM 6057E from Wacker Silicones Corporation; Trimethylsilylamodimethicone available as SF1708-D1, SM201 and SM2115-D2 from Costec, Inc. Dow Corning® Q2-7224 and Q2-8220 from Dow Corning Corp. and L653, 655, 656 and ADM 3047E from Wacker Silicones Corporation.

Indicative of the class of silicone polyglucosides is Octyl Dimethicone Ethoxy Glucoside (SPG 128) from Wacker Silicones Corporation.

Polyether functionalized silicones are typified by Dimethicone Copolyol available as SF 1188 from Costec, Inc. Dow Corning® 2501, 3225C, Q2-5324 and Q2-5434 from Down Corning Corp. and DMC 6032 and Cetyl Dimethicone Copolyol available as CMC 3071 from Wacker Silicones Corporation.

The above listings are representative and any polydiorganosiloxane polymer fluid functional for use in adjusting the adhesive properties of a pressure-sensitive adhesive may be utilized.

With reference to Formula I, preferably R is methyl and the diorganopolysiloxane is a dimethylpolysiloxane polymer generically known as dimethicone. Therefore the terms "polydimethylsiloxane" and "dimethicone" are used interchangeably and refer to the preferred diorganopolysiloxane polymer. Various grades or weights of dimethicone may be referred to in the examples under the trade name Dimethicone "XXX" where "XXX" is indicative commercially of the viscosity of the polysiloxane polymer.

In reference to the preferred embodiment, polydimethylsiloxanes (dimethicones), are silicone oils consisting of a mixture of fully methylated linear siloxane polymers having the formula:

$$(H_3C)_3Si-O-[(CH_3)_2Si-O-]_nSi(CH_3)_3.$$

where n is an integer sufficient to provide a fluid having a viscosity that increases with degrees of polymerization, ranging from about 20 to 25,000 and preferably from 20 to 12,500, centistokes. They are widely used in the formulation of cosmetic and personal care products to protect, soothe or beautify the skin, hair and nails, especially to enhance the skin feeling and quality (softness and smoothness) but have not heretofore been known to moderate adhesive properties of pressure sensitive adhesives.

The adhesion and tackiness for transdermal devices and particularly the matrix type patches are very important factors, especially when the patches are applied to an area with sensitive skin, such as the face. The purpose of using dimethicone in this invention is as an adhesive altering agent in a pressure-sensitive adhesive to control the tackiness and adhesiveness of the patch to the skin, making it easy to peel off the skin surface without causing damage or irritation and without leaving adhesive residue.

Irritation to the skin from the application of matrix pressure sensitive adhesive matrix type patches is the result of a wide range of adverse skin reactions resulting from the presence of chemicals or other irritants as well as other factors including the mechanical force required to remove the adhesive from the skin. Typically, the adverse skin reactions are primary skin irritation reactions that result in localized inflammation or injury.

Glycerine is known in the areas of skin care and transdermal drug delivery for use as an emollient, such as taught by U.S. Pat. No. 4,687,481, and as an anti-irritant, as taught by U.S. Pat. No. 4,855,294. Glycerine is also known to modulate the delivery of drugs transdermally as taught by W. E. Heiber et al., "Use of Glycerin in Moderating Transdermal Drug Delivery," WO 93/25168, published Dec. 23, 1993. However, the combination of glycerine with vitamins C and E, along with an adhesion-adjusting agent, in a pressure-sensitive adhesive matrix patch to promote anti-wrinkling in damaged skin and, concurrently provide an adhesive that is easily removed without causing skin irritation or leaving behind unwanted adhesive residue is not heretofore known or suggested.

Example I

A two week efficacy study was conducted by using anti-wrinkle matrix patches formulated according to this example. A total of 31 female volunteers, aged from 35 to 60 years, applied the patches overnight, every other night for two weeks to an area of the skin adjacent the eyes showing signs of wrinkling. A scoring, where a rating of 5 indicated deep wrinkles and a rating of 0 indicated no wrinkles, was made one hour after patch removal.

| Formulation | Composition (%, w/w) |
|---|---|
| Duro-Tak 87-2979* | 86.5 |
| Dimethicone 350, NF** | 7.5 |
| Glycerine, USP | 5.0 |
| L-Ascorbic Acid 6-Palmitate, USPNF | 0.5 |
| Vitamin E, USP | 0.5 |

*Acrylic copolymer pressure-sensitive adhesive
**Polydimethylsiloxane having a viscosity of 350 centistokes The results show that the scoring decreased from a baseline of 2.3±0.92 to 1.2±0.83 within two weeks, indicating that the anti-wrinkle patches were effective in minimizing the fine lines/wrinkles.

The following examples show anti-wrinkle formulations that can be utilized in the same manner as those in Example I.

Example II

| Formulation | Composition (%, w/w) |
|---|---|
| Duro-Tak 87-2979* | 70–85 |
| Dimethicone 200** | 0.1–10 |
| Glycerine | 0.1–10 |
| L-Ascorbic Acid 6-Palmitate | 0.1–10 |
| Vitamin E | 0.1–10 |
| Vitamin A Palmitate | 0.1–10 |
| Salicylic acid | 0.1–5 |

*Acrylic copolymer pressure-sensitive adhesive
**Polydimethylsiloxane having a viscosity of 200 centistokes Example III

| Formulation | Composition (%, w/w) |
|---|---|
| Duro-Tak 87-2516* | 70–85 |
| Dimethicone 500** | 0.1–10 |
| Glycerine | 0.1–10 |
| L-Ascorbic Acid 6-Palmitate | 0.1–10 |
| Vitamin E | 0.1–10 |
| Vitamin A Palmitate | 0.1–10 |
| Salicylic acid | 0.1–5 |

*Acrylic copolymer pressure-sensitive adhesive
**Polydimethylsiloxane having a viscosity of 500 centistokes Example IV

| Formulation | Composition (%, w/w) |
|---|---|
| Duro-Tak 87-2196* | 70–85 |
| Dimethicone 20** | 0.1–10 |
| Glycerine | 0.1–10 |
| L-Ascorbic Acid 6-Palmitate | 0.1–10 |
| Vitamin E | 0.1–10 |
| Vitamin A Palmitate | 0.1–10 |
| Salicylic acid | 0.1–5 |

*Acrylic copolymer pressure-sensitive adhesive
**Polydimethylsiloxane having a viscosity of 20 centistokes

Example V

| Formulation | Composition (%, w/w) |
|---|---|
| Nacor 72-9965* | 70–85 |
| Dimethicone 1000** | 0.1–10 |
| Glycerine | 0.1–10 |
| L-Ascorbic Acid 6-Palmitate | 0.1–10 |
| Vitamin E | 0.1–10 |
| Vitamin A Palmitate | 0.1–10 |
| Salicylic acid | 0.1–5 |

*Waterborne acrylic copolymer pressure-sensitive adhesive
**Polydimethylsiloxane having a viscosity of 1000 centistokes

Example VI

| Formulation | Composition (%, w/w) |
|---|---|
| Nacor 72-8725* | 70–85 |
| Dow Corning Q2-5200** | 0.1–10 |
| Glycerine | 0.1–10 |
| L-Ascorbic Acid 6-Palmitate | 0.1–10 |
| Vitamin E | 0.1–10 |
| Vitamin A Palmitate | 0.1–10 |
| Salicylic acid | 0.1–5 |

*Waterborne rubber-based pressure-sensitive adhesive
**Lauryl dimethicone having a viscosity of 5200 centistokes

Example VII

| Formulation | Composition (%, w/w) |
|---|---|
| Duro-Tak 36-6172* | 70–85 |
| Dow Corning 345** | 0.1–10 |
| Glycerine | 0.1–10 |
| L-Ascorbic Acid 6-Palmitate | 0.1–10 |
| Vitamin E | 0.1–10 |
| Vitamin A Palmitate | 0.1–10 |
| Salicylic acid | 0.1–5 |

*Waterborne rubber-based pressure-sensitive adhesive
**Cyclomethicone having a viscosity of 345 centistokes

Example VIII

| Formulation | Composition (%, w/w) |
|---|---|
| Duro-Tak 34-4230* | 70–85 |
| DMC 3071** | 0.1–10 |
| Glycerine | 0.1–10 |
| L-Ascorbic Acid 6-Palmitate | 0.1–10 |
| Vitamin E | 0.1–10 |
| Vitamin A Palmitate | 0.1–10 |
| Salicylic acid | 0.1–5 |

*Rubber-based hot melt pressure-sensitive adhesive
**Cetyl dimethicone having a viscosity of 3071 centistokes

Example IX

| Formulation | Composition (%, w/w) |
|---|---|
| PIB 500/Poly butyl 100 (34/66, % w/w)* | 70–85 |
| Dimethicone 350** | 0.1–10 |
| Glycerine | 0.1–10 |
| L-Ascorbic Acid 6-Palmitate | 0.1–10 |
| Vitamin E | 0.1–10 |
| Vitamin A Palmitate | 0.1–10 |
| Salicylic acid | 0.1–5 |

*Polyisobutylene rubber emulsion pressure-sensitive adhesive
**Polydimethylsiloxane having a viscosity of 350 centistokes

Example X

| Formulation | Composition (%, w/w) |
|---|---|
| EVA-TAK 33-4060* | 70–85 |
| PDM 1000** | 0.1–10 |
| Glycerine | 0.1–10 |
| L-Ascorbic Acid 6-Palmitate | 0.1–10 |
| Vitamin E | 0.1–10 |
| Vitamin A Palmitate | 0.1–10 |
| Salicylic acid | 0.1–5 |

*Waterborne ethylene vinyl acetate pressure-sensitive adhesive
**Phenyltrimethicone having a viscosity of 1000 centistokes

Example XI

| Formulation | Composition (%, w/w) |
|---|---|
| Robond PS-20* | 70–85 |
| DMC 6032** | 0.1–10 |
| Glycerine | 0.1–10 |
| L-Ascorbic Acid 6-Palmitate | 0.1–10 |
| Vitamin E | 0.1–10 |
| Vitamin A Palmitate | 0.1–10 |
| Salicylic acid | 0.1–5 |

*Water-based acrylic pressure sensitive adhesive
**Dimethicone Copolyol Acetate having a viscosity of 6032 centistokes

Example XII

| Formulation | Composition (%, w/w) |
|---|---|
| Nacor 72-9965* | 70–80 |
| Dimethicone 350** | 0.1–10 |
| Glycerine | 0.1–10 |
| Herbs/botanic Extracts*** | 0.1–15 |
| L-Ascorbic Acid 6-Palmitate | 0.1–10 |
| Vitamin E | 0.1–10 |
| Vitamin A Palmitate | 0.1–10 |
| Salicylic Acid | 0.1–5 |

*Waterborne acrylic copolymer pressure-sensitive adhesive
**Polydimethylsiloxane having a viscosity of 350 centistokes
***For example: Algae, Aloe vera, Cucumber, Ginseng, Ginkgo biloba and Hibiscus.

Example XIII

| Formulation | Composition (%, w/w) |
|---|---|
| Duro-Tak 87-2979* | 70–85 |
| Dimethicone 12,500** | 0.1–10 |
| Glycerine | 0.1–10 |
| L-Ascorbic Acid 6-Palmitate | 0.1–10 |
| Vitamin E | 0.1–10 |
| Vitamin A Palmitate | 0.1–10 |
| α-Hydroxy Acids*** | 0.1–5 |

*Acrylic copolymer pressure-sensitive adhesive
**Polydimethylsiloxane having a viscosity of 12,500 centistokes
***For example: Citric acid, Glycolic acid, Lactic acid and Malic acid.

Example XIV

| Formulation | Composition (%, w/w) |
|---|---|
| Duro-Tak 87-2516* | 70–85 |
| Dimethicone 350** | 0.1–10 |
| Glycerine | 0.1–10 |
| L-Ascorbic Acid 6-Palmitate | 0.1–10 |
| Vitamin E | 0.1–10 |
| Vitamin A Palmitate | 0.1–10 |
| Salicylic acid | 0.1–5 |
| Hyaluronic acid | 0.1–5 |

*Acrylic copolymer pressure sensitive adhesive
**Polydimethylsiloxane having a viscosity of 350 centistokes

Example XV

| Formulation | Composition (%, w/w) |
|---|---|
| Duro-Tak 87-2979* | 70–85 |
| Dimethicone 350** | 0.1–10 |
| Glycerine | 0.1–10 |
| L-Ascorbic Acid 6-Palmitate | 0.1–10 |
| Vitamin E | 0.1–10 |
| Vitamin A Palmitate | 0.1–10 |
| Salicylic acid | 0.1–5 |
| Caffeine | 0.1–5 |

*Acrylic copolymer pressure sensitive adhesive
**Polydimethylsiloxane having a viscosity of 350 centistokes These examples are not intended to be limiting in scope but are intended to be representative of formulations containing a Vitamin C ester, Vitamin E, glycerine and an added polydiorganosiloxane adhesion altering member to a pressure-sensitive adhesive to provide an anti-wrinkle matrix-type device. Other than functionality, the only limitation to the combination of ingredients is that the components must be dissolved in the adhesive carrier. As such, the adhesive device will provide for effective treatment in removing fine line wrinkles during the treatment period without causing skin irritation and can be easily removed.

What is claimed is:

1. A transdermal delivery device for delivering an effective amount of an antioxidant combination of a fat soluble Vitamin C ester and Vitamin E to the skin of a subject for the treatment of wrinkles, said device comprising an impermeable backing layer and a pressure sensitive adhesive layer for adhering the device to the skin of the subject, said pressure-sensitive adhesive layer comprising from about 60 to about 99.5% by weight of a pressure sensitive adhesive selected from the group consisting of acrylic copolymers, rubber-based adhesives and ethylene vinyl acetate copolymers and having dissolved therein about 0.1 to about 10% by weight of each of the following: a fat soluble Vitamin C ester, Vitamin E, glycerine, and a polydiorganosiloxane polymer adhesion adjusting agent.

2. The transdermal delivery device of claim 1, wherein the weight ratio of Vitamin C ester to Vitamin E is between about 0.1:10 to 10:1.

3. The transdermal delivery device of claim 1, wherein the fat soluble Vitamin C ester is L-Ascorbic Acid 6-Palmitate.

4. The transdermal delivery device of claim 1, wherein the polydiorganosiloxane has the formula:

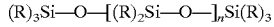

where R is a hydrocarbon or substituted hydrocarbon of 1 to about 20 carbon atoms and n is an integer sufficient to cause said polydiorganosiloxane to have a viscosity of between about 20 and 25,000 centistokes.

5. The transdermal delivery device of claim 4, wherein R is a member having 1 to about 20 carbon atoms selected from the group consisting of alkyl, aryl, and cycloalkyl which are unsubstituted or contain halogen, amino, hydroxy or ether functionalities.

6. The transdermal delivery device of claim 5, wherein R is methyl and said polydiorganosiloxane is a fully methylated linear polydimethyl siloxane polymer having the formula:

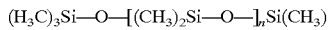

where n is an integer sufficient to cause said polydimethylsiloxane to have a viscosity of between about 20 and 25,000 centistokes.

7. The transdermal delivery device of claim 6, wherein n is an integer sufficient to cause said polydimethylsiloxane to have a viscosity of between about 20 and 12,500 centistokes.

8. The transdermal delivery device of claim 6, further containing in said pressure-sensitive adhesive layer from 0.1 to 10% by weight of one or more additional ingredients selected from the group consisting of α and β hydroxy acids, 2-pyrrolidone-5-carboxylic acid, Vitamin A, salicylic acid and its salts, caffeine, hyaluronic acid, herbs and botanic extracts with the proviso that the total concentration of said additional ingredients must be dissolved in said pressure sensitive adhesive.

9. The transdermal delivery device of claim 8, wherein said additional ingredient is vitamin A.

10. The transdermal delivery device of claim 6, wherein said pressure sensitive adhesive is an acrylic copolymer.

11. The transdermal delivery device of claim 6, wherein said pressure sensitive adhesive is a rubber-based adhesive.

12. A method for the transdermal reduction of fine line wrinkles on the skin of a subject comprising applying to the wrinkled area of the skin of the subject a pressure sensitive adhesive patch consisting of an impermeable backing having adhered thereto a pressure sensitive adhesive layer wherein said pressure sensitive layer is adhered to the skin during a treatment period wherein said pressure-sensitive adhesive layer comprises from about 60 to about 99.5% by weight of a pressure sensitive adhesive selected from the group consisting of acrylic copolymers, rubber-based adhesives and ethylene vinyl acetate copolymers and has dissolved therein about 0.1 to about 10% by weight of each of the following: a fat soluble Vitamin C ester, Vitamin E, glycerine, and a polydiorganosiloxane polymer adhesion adjusting agent.

13. The method of claim 12, wherein the weight ratio of fat soluble Vitamin C ester to Vitamin E is between about 0.1:10 to 10:0.1.

14. The method of claim 12, wherein the fat soluble Vitamin C ester is L-Ascorbic Acid 6-Palmitate.

15. The method of claim 12, wherein the polydiorganosiloxane has the formula:

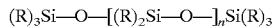

where R is a hydrocarbon or substituted hydrocarbon of 1 to about 20 carbon atoms and n is an integer sufficient to cause said polydiorganosiloxane to have a viscosity of between about 20 and 25,000 centistokes.

16. The method of claim 15, wherein R is a member having 1 to about 20 carbon atoms selected from the group consisting of alkyl, aryl, and cycloalkyl which are unsubstituted or contain halogen, amino, hydroxy or ether functionalities.

17. The method of claim 16, wherein R is methyl and said polydiorganosiloxane is a fully methylated linear polydimethyl siloxane polymer having the formula:

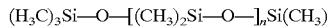

where n is an integer sufficient to cause said polydimethylsiloxane to have a viscosity of between about 20 and 25,000 centistokes.

18. The method of claim 17, wherein n is an integer sufficient to cause said polydimethylsiloxane to have a viscosity of between about 20 and 12,500 centistokes.

19. The method of claim 17, further containing in said pressure-sensitive adhesive layer from 0.1 to 10% by weight of one or more additional ingredients selected from the group consisting of α and β hydroxy acids, 2-pyrrolidone-5-carboxylic acid, Vitamin A, salicylic acid and its salts, caffeine, hyaluronic acid, herbs and botanic extracts with the proviso that the total concentration of said additional ingredients must be dissolved in said pressure sensitive adhesive.

20. The method of claim 19, wherein said additional ingredient is vitamin A.

21. The method of claim 17, wherein said pressure sensitive adhesive is an acrylic copolymer.

22. The method of claim 17, wherein said pressure sensitive adhesive is a rubber-based adhesive.

* * * * *